United States Patent [19]

Hordvik

[11] 4,091,681

[45] May 30, 1978

[54] METHOD FOR THE SIMULTANEOUS DETERMINATION OF LOW OPTICAL BULK AND SURFACE ABSORPTION COEFFICIENTS IN SOLIDS

[75] Inventor: Audun Hordvik, Trondheim, Norway

[73] Assignee: The United States of America as represented by the Secretary of the Air Force, Washington, D.C.

[21] Appl. No.: 808,495

[22] Filed: Jun. 21, 1977

[51] Int. Cl.$^2$ .............................................. G01H 1/00
[52] U.S. Cl. ................................ 73/574; 331/94.5 R; 331/DIG. 1
[58] Field of Search ............... 73/557, 67.2, 67.5 R, 73/71.3, 24; 250/341, 343, 345, 347; 356/97; 331/94.5 R, DIG. 1

[56] References Cited

U.S. PATENT DOCUMENTS

| | | | |
|---|---|---|---|
| 3,700,890 | 10/1972 | Kruezer | 250/341 |
| 3,899,921 | 8/1975 | Hockley | 73/67.2 |
| 3,938,365 | 2/1976 | Dewey | 73/24 |

*Primary Examiner*—Richard C. Queisser
*Assistant Examiner*—Stephen A. Kreitman

*Attorney, Agent, or Firm*—Joseph E. Rusz; Jacob N. Erlich

[57] ABSTRACT

A photoacoustic method of simultaneously determining optical bulk and surface absorption coefficients in solids in which a transducer is attached to the solid for measuring the amplitude of the acoustic wave generated by a beam of incident radiation as a function of distance of the transducer to the incident beam at a wavelength where bulk and surface losses, respectively, are heavily dominant. The transducer is chosen so as to give different functional dependencies for the bulk and surface absorption curves, respectively. The solid sample is also calibrated at wavelengths where bulk and surface absorption, respectively, are known. The output versus position or distance is measured at the wavelength of interest, and values of surface and bulk absorption coefficients are fitted to the respective pure curves so that they will add up to the experimentally generated composite curve. After the bulk and surface absorption curves have been determined for the wavelength of interest, the values of bulk and surface absorption coefficients can be determined by using the calibration constants found earlier.

4 Claims, 5 Drawing Figures

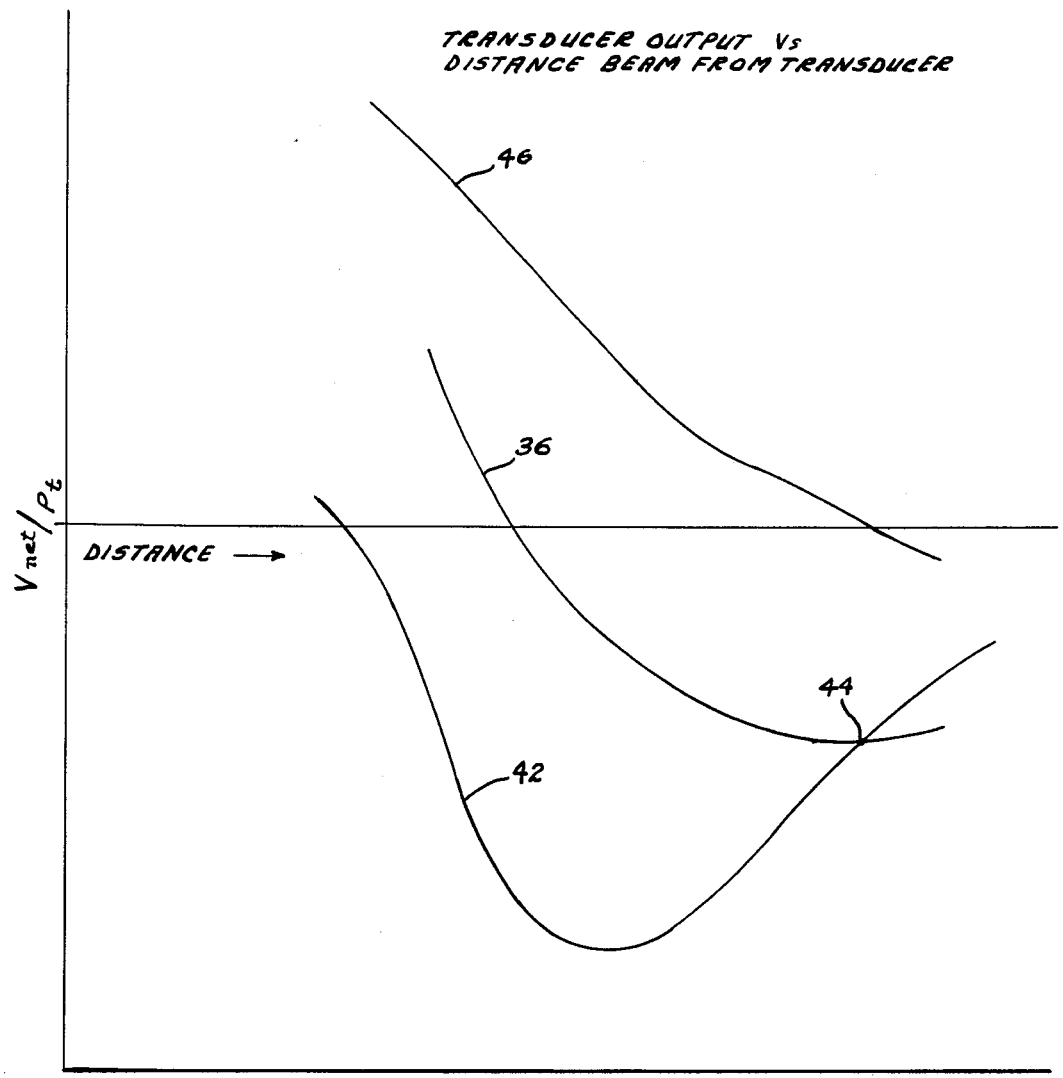

METHOD FOR THE SIMULTANEOUS DETERMINATION OF LOW OPTICAL BULK AND SURFACE ABSORPTION COEFFICIENTS IN SOLIDS

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a method of measuring absorption coefficients, and, more particularly to a method of simultaneously measuring low optical bulk and surface absorption in solids.

Knowledge of bulk and surface absorption in an optical material is necessary when determining the materials applicability in certain optical systems. For example, high power lasers presently under development require high power laser windows made of optical materials which possess both low bulk and surface absorption properties. If the improper optical material is utilized in the high power lasers, the final result will be one of the following: (a) catastrophic failure of the window, for example, from the various thermomechanical effects which are different from each material and for each cooling configuration; (b) window fracture due to the thermal stresses from the nonuniform distribution of temperature induced by the laser; (c) spontaneous cleavage which occurs unpredictably; (d) permanent crosshatch distortion; and (e) the most difficult to detect, thermal lensing, which distorts the optical quality of the window but does not permanently damage the physical structure thereof.

Optical absorption is known to depend upon material purity, material preparation and component fabrication techniques. By measuring both the bulk and surface absorption spectrum of a solid important information is obtained concerning the structure and purity content of the solid both of which are of utmost importance in determining a material's use in optical and electronic application. In addition such information can give clues to what steps must be taken to lower the optical absorption coefficient if desired.

Most of the conventional techniques for determining optical absorption measure the combined effect of surface and bulk losses. However, to identify the cause of the absorption, it is necessary to separate the two components and determine the value of each. A few methods have been developed for measuring both surface and bulk absorption, but these techniques require either several samples or special large sample sizes and have encountered numerous problems. For example, with prior techniques, if either one of the surface or bulk absorption was substantially greater than the other, it was virtually impossible to determine the smaller absorption. Likewise, if the surface and bulk absorption were substantially identical, accurate measurements of individual surface and bulk absorptions were virtually impossible. In addition, methods heretofore in existence have been found less than desirable for the determination of the very low absorption coefficients needed in optical materials which are incorporated into high power laser systems. Since in recent years substantial progress has been made in the fabrication of low loss optical materials for the visible and infrared, it is essential that new techniques be provided which are capable of measuring in an economical and reliable fashion bulk absorption in the $1 \times 10^{-4}$ cm$^{-1}$ to $1 \times 10^{-6}$ cm$^{-1}$ range.

SUMMARY OF THE INVENTION

The instant invention overcomes the problems set forth hereinabove by providing a technique which utilizes piezoelectric transducers to measure simultaneously optical bulk and surface absorption coefficients in solids. In addition, the method of this invention is capable of determining extremely low bulk and surface absorption coefficients, as well as reliably measuring the bulk and surface absorption when either bulk or surface absorption is substantially greater than the other or when they are virtually the same.

The instant invention provides a procedure whereby only a single small sample is required during the experimentation, and, since A.C. instead of the conventional D.C. detection approach is utilized, the method of this invention is much more sensitive than previous approaches.

The method of this invention for simultaneously determining the optical bulk and surface absorption coefficients in solids utilizes an experimental arrangement made up of a continuous wave laser, a beam chopper, the solid sample under investigation, a transducer attached to the sample for measuring the amplitude of the generated acoustic wave, an unattached transducer adjacent the sample to detect any signal generated by scattered radiation, a power meter to measure the laser power, and a phase sensitive detection system for measuring the output of the attached transducer.

A periodically interrupted light beam emanating from the laser, is incident on the solid sample to be tested. The absorbed radiation causes heating and thus expansion of the sample, and an acoustic or elastic wave is generated, the amplitude of which is proportional to the absorbed energy. The induced elastic wave is detected with the piezoelectric transducer which is attached to the sample, and the transducer output is monitored with the phase sensitive detection system.

The experimental configuration set forth hereinabove allows both surface and bulk absorption coefficients to be determined simultaneously by the method of this invention. By properly choosing the sign and magnitude of the piezoelectric constant of the transducer ceramic, the signal generated by bulk absorption is 180° out of phase with the signal generated by surface absorption. Further, if the output voltage is measured as a function of the distance between the laser beam and the transducer, the curves generated by pure bulk absorption and pure surface absorption, have quite different functional dependencies. The reason for different characteristic shapes of the bulk and surface absorption curves is that an acoustic wave generated on the surface acts approximately as a spherical wave having components which interact differently with the transducer than does a bulk generated acoustic wave which propagates with nearly radial symmetry.

The procedure of the instant invention is summarized as follows: After the appropriate transducer has been selected and attached to the sample, the functional dependencies of the output versus distance curves for pure bulk and pure surface absorption curves are determined by making measurements at wavelengths where respectively bulk and surface losses are heavily dominant. The sample must also be calibrated by conventional means at wavelengths where respectively bulk and surface absorption are known. The calibration can usually be done simultaneously with the generation of the bulk and surface absorption curves. The output versus position curve is now measured at the wavelength of interest, and values of surface and bulk absorption coefficients are fitted to the respective "pure" curves so that they will add up to the experimentally generated composite curve. The curve fitting process can be greatly simplified when, as is the case in the instant invention, the bulk absorption curve goes through zero. At the "zero-crossing" only surface absorption is observed, and the whole surface absorption curve can be generated since its functional dependence is known. The bulk absorption curve can then be found by subtraction. After the bulk and surface absorption curves have been determined for the particular wavelength of interest, the values of bulk and surface absorption coefficients can be determined by using the calibration constants found earlier.

It is therefore an object of this invention to provide a method for simultaneously measuring the optical bulk absorption coefficient and surface absorption coefficient in solids.

It is another object of this invention to utilize a piezoelectric transducer to measure the magnitude and phase of the elastic wave generated by surface and bulk absorption.

It is still another object of this invention to provide curves generated by measuring the output versus distance between transducer and incident beam for pure surface and pure bulk absorption, respectively, which will be sufficiently different to allow both surface and bulk absorption to be determined by curve fitting.

It is still a further object of this invention to provide a method of simultaneously determining optical bulk and surface absorption coefficients in solids by apparatus which is economical to produce and reliable in operation.

For a better understanding of the present invention, together with other and further objects thereof, reference is made to the following description taken in connection with the accompanying drawing and its scope will be pointed out in the appended claims.

DESCRIPTION OF THE DRAWING

FIG. 5 is a graph illustrative of $V_{out}/P_t$ versus distance for an experimentally determined curve having the combination of bulk absorption and surface absorption as well as the pure bulk and pure surface absorption curves derived therefrom by the method of this invention.

DETAILED DESCRIPTION OF THE PREFERRED EMBODIMENT

Figure 1:
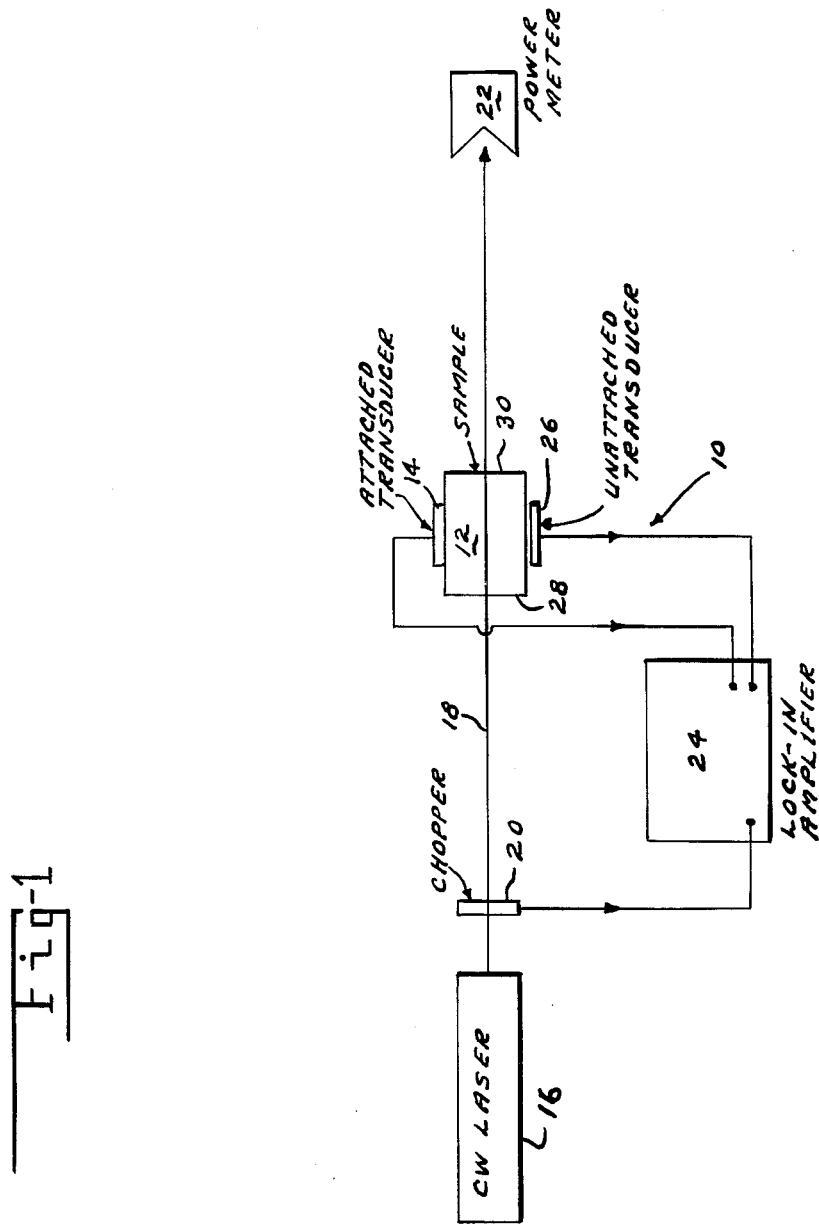
FIG. 1 is a schematic representation of the experimental apparatus utilized in the method of this invention for simultaneously determining low bulk and surface absorption coefficients in solids.

Reference is now made to FIG. 1 of the drawing which best shows the apparatus 10 utilized in the technique of this invention for simultaneously determining low optical bulk and surface absorption coefficients in a solid. Any suitable solid sample 12 whose bulk and surface absorptions are to be determined at a particular wavelength of interest is operatively connected to apparatus 10. The specific elements which make up test apparatus 10 are enumerated hereinbelow.

A conventional piezoelectric transducer 14 is attached to sample 12 while a continuous wave laser 16 of a preselected wavelength is situated adjacent sample 10 so as to focus the laser beam 18 emanating therefrom on sample 12. Interposed between laser 16 and sample 12 is a conventional beam chopper 20. A conventional power meter 22 is located adjacent sample 12 on the side of sample 12 opposite laser 16 to measure the laser power passing therethrough, while a conventional phase sensitive detection system 24 in the form of a lock-in-amplifier is operatively connected to transducer 14 for measuring the output of transducer 14.

When the piezoelectric transducer 14 is illuminated by light beam 18, an electrical signal is generated due to heating. In case sample 12 scatters part of laser beam 18 onto transducer 14, an electrical signal is generated in transducer 14 due to heating, and it may be necessary to correct for the contribution of scatter to the output signal. This is accomplished by placing a second transducer 26 in the immediate vicinity of sample 12 and symmetrically with respect to laser beam 18. Transducer 26 is not in acoustical contact with sample 12, but will pick up scattered radiation. The output from transducer 26 is subtracted from the output from transducer 14 to correct for scatter. In addition, baffles (not shown) should be placed in front of both transducers 14 and 26 to shield them from incoming radiation beam 18.

Sample 12 is made of any solid material which is to be tested and is preferably in the shape of a parallelepiped, but other configurations can be used provided there is a sufficiently large flat surface for attaching transducer 14. The input and output surfaces 28 and 30, respectively, should preferably be flat and polished and for convenience parallel to minimize beam refraction and scatter. A typical sample dimension would be 5 × 10 × 12 mm. With the instant method, transducer 14 is attached to one of the 10 × 12 mm surfaces and beam 18 is incident perpendicularly on either a 5 × 10 mm or 5 × 12 mm surface.

Figure 2:
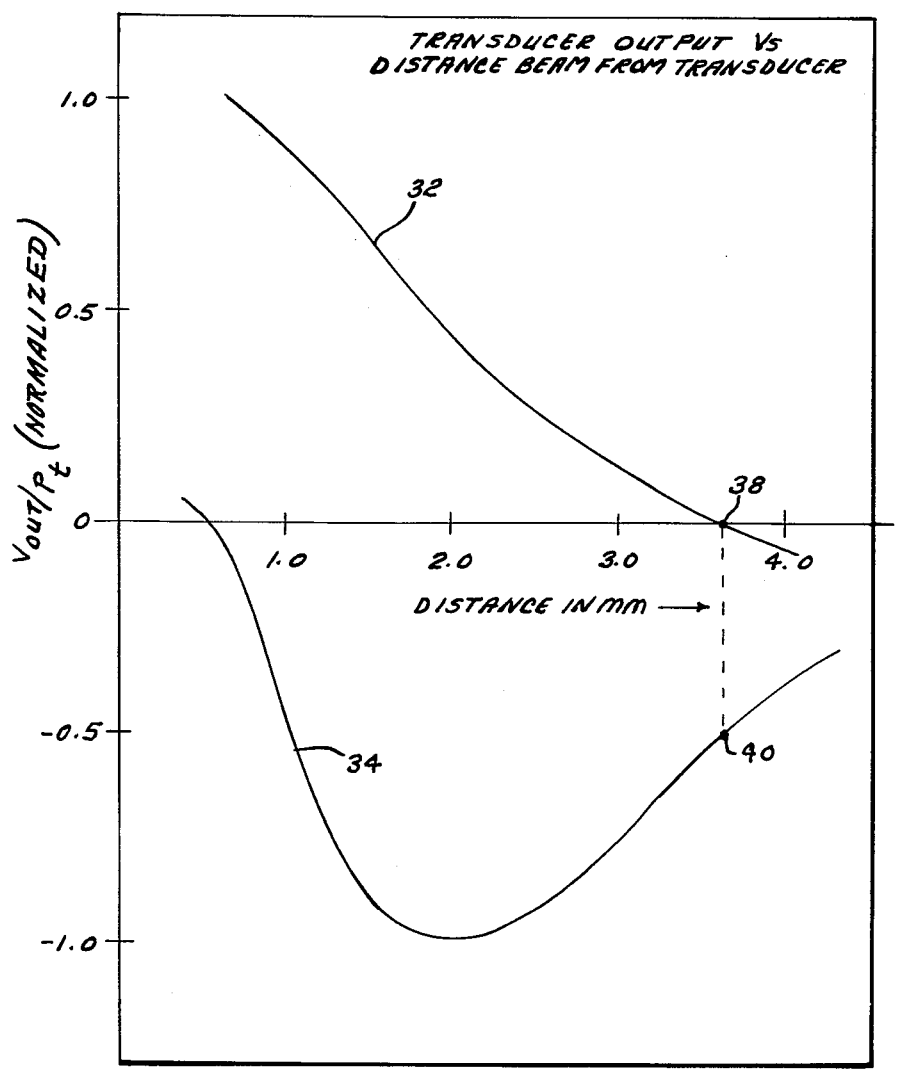
FIG. 2 is a graph illustrative of $V_{out}/P_t$ versus distance of curves generated for pure bulk and surface absorption of a solid sample at wavelengths at which the bulk and surface absorption, respectively, are dominant.

Piezoelectric transducer 14 is attached to sample 12 by any conventional epoxy adhesive. It is essential that in the method of this invention transducers 14 and 26 be selected such that they will yield outputs which produce surface and bulk absorption curves, respectively, as shown in FIG. 2 of the drawing, which have been different functional dependencies or shapes. As shown in FIG. 2, the bulk absorption curve 32 and the surface absorption curve 34 are defined by the output signal or voltage/power versus the distance between laser beam 18 and transducer 14. Although this requirement can be satisfied in a variety of ways, the particular apparatus 10 set forth hereinabove produces extremely desirable test results and therefore accurate readings of extremely low optical bulk and surface absorption coefficients.

Figure 3:
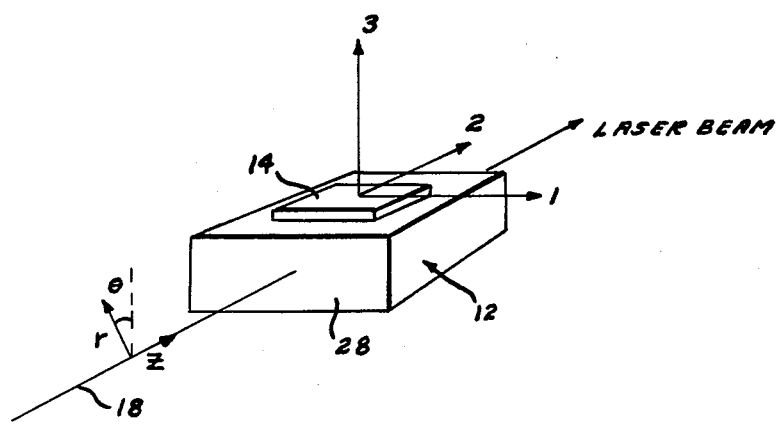
FIG. 3 is a pictorial representation of the sample and a transducer attached thereto utilized in the method of the instant invention.

Transducer 14 chosen for the method of the instant invention, was made from the piezoelectric ceramic lead titanate zirconate which is commerically available under the brand name PZT. There are several types of this material, an example of one being PZT-5H. A typical exmple of the dimensions of transducer 14 are 0.250 × 0.250 × 0.100 inches. The two 0.250 × 0.250 inch surfaces are electroplated, and as best shown in FIG. 3, transducer 14 is poled perpendicularly to the same surfaces. With the axes labelled as in FIG. 3 where the 3-axis is along the direction of poling, transducer 14 has three independent piezoelectric constants $g_{33}$, $g_{31}$ and $g_{15}$ of which only $g_{33}$ and $g_{31}$ are of interest here. For PZT-5H one has $g_{33} = 19.7 \times 10^{-3}$ volt meter/Newton and $g_{31} = g_{32} = -9.1 \times 10^{-3}$ volt meter/Newton. The output voltage from transducer 14 is proportional to $(g_{33} \sigma_{33} + g_{31}(\sigma_{31} + \sigma_{32}))$ where $\sigma_{ij}$ are the induced stresses. For the apparatus 10 used with the instant invention one finds that for bulk absorption the term associated with $g_{31}$ will be the dominant one, at least for shorter distances between beam 18 and transducer 14. However, for surface absorption the term associated with $g_{33}$ is largest, and it has the opposite sign of the $g_{31}$ term.

The configuration 10 of this invention allows both surface and bulk absorption coefficients to be determined simultaneously. By properly choosing the sign and magnitude of the piezoelectric constants of the transducer ceramic, as was for example done hereinabove, the signal generated by bulk absorption is 180° out of phase with the signal generated by surface absorption. Further, if the output voltage is measured as a function of the distance between laser beam 18 and transducer 14, the curves 32 and 34, respectively, generated by pure bulk absorption and pure surface absorption, have quite different functional dependencies. The reason for different characteristic shapes of the bulk and surface absorption curves 32 the 34 is that an acoustic wave generated on the surface of sample 12 acts approximately as a spherical wave having components which interact different with transducer 14 than does a bulk acoustic wave which propagates with nearly radial symmetry. The bulk absorption curve 32 has its maximum at transducer 14 and the output falls off rapidly as the distance from transducer 14 increases. About ⅔ of the way across sample 12 the output is zero, and it then changes sign at larger distances. This effect is caused by the reflections from the surface opposite transducer 14. The surface absorption curve 34 is 180° out of phase with bulk absorption curve 32 across most of sample 12, and it has its maxiumum at some distance from transducer 14.

Figure 4:
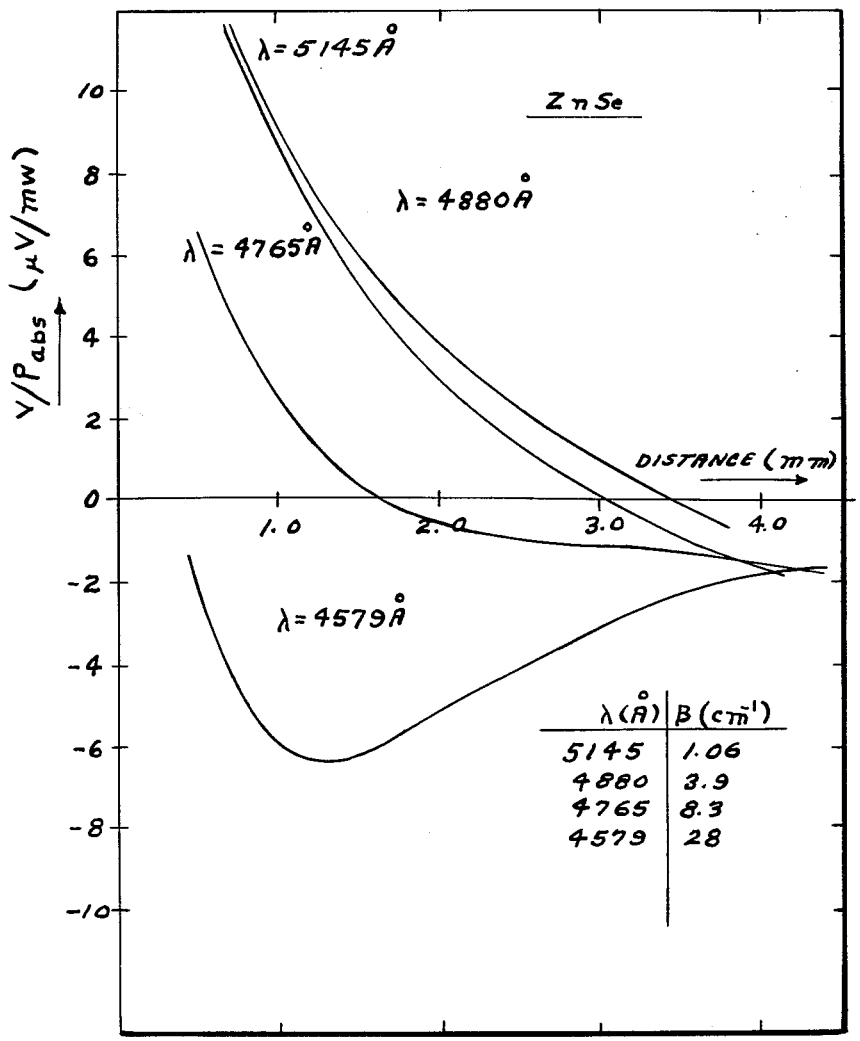
FIG. 4 is a graph illustrative of $V_{out}/P$ versus distance for a CVD ZnSe sample at various wavelengths near the electronic absorption edge.

An example of transducer response for surface and bulk loss can easily be illustrated by measuring absorption in a semiconductor at several frequencies both below and above the electronic band gap. In FIG. 4, for example, it shows transducer output voltage per unit of absorbed power versus beam to transducer distance for a CVD ZnSe sample for different wavelengths near the electronic absorption edge. At 5145 A ($\beta = 1$ cm$^{-1}$) the sample acts essentially as a bulk absorber while at 4579 A ($\beta \times 28$ cm$^{-1}$) almost all incident energy is absorbed in the first millimeter. This latter case is thus equivalent to surface absorption behavior. As is evident from FIG. 4, the shape of the curves change drastically depending upon whether bulk or surface loss dominate the overall optical absorption.

In principle, the absorption coefficient can be calculated from the measured amplitude of the acoustic wave; however, this calculation is inaccurate due to uncertainty in the coupling between sample 12 and transducer 14. Instead, each sample 12 is calibrated at a wavelength of known absorption. The calibration must be done separately for bulk and surface absorption. For bulk absorption, calibration is most conveniently performed at a wavelength where $\beta$ can be measured by transmission, while for surface absorption it is done in an opaque region of the material. Since the generated voltage is proportional to the absorbed energy, the calibration constants can readily be used to determine the absorption at any desired wavelength.

The procedure followed in the instant invention for measuring both low bulk and surface absorption coefficients is to:

(1) Select a transducer 14 which will give bulk and surface absorption curves, 32 and 34, respectively, as shown in FIG. 2 of the drawing which have very different functional dependencies or shapes. Preferably, at least one curve (as shown in FIG. 2) should go through zero at a position where the other curve still has a substantial value.

(2) Set up the apparatus 10 shown in FIG. 1 of the drawing and as set forth in detail hereinabove.

(3) Select a wavelength for laser beam 18 at which it can be determined by some conventional means that the bulk absorption is by far the dominant absorption mechanism. Such is usually the case in a region where $\beta$ is between 2 cm$^{-1}$ to 10$^{-2}$ cm$^{-1}$. ($\beta$ = bulk absorption coefficient)

(4) The functional dependence (shape) of the bulk absorption curve 32 is now determined. This is accomplished by measuring the output voltage from detection system 24 versus the distance from beam 18 to transducer 14 and simultaneously monitoring the transmitted power, $P_t$, with power meter 22. A plot of output voltage/transmitted power (Vout/$P_t$) as a function of distance is shown in FIG. 2.

(5) Determine a calibration factor for bulk absorption which is to be utilized hereinbelow. This step can be performed simultaneously with the measurements made in step (4). While step (4) does not require an accurate knowledge of the absorption coefficient, step (5) does. The bulk absorption coefficient $\beta$ must be determined at a convenient wavelength, that is, in a region where the surface absorption can be neglected. The determination of the absorption coefficient $\beta$ is made at a convenient wavelength by conventional procedures, which means that $\beta$ must be fairly large, typically in the 2 cm$^{-1}$ to 10$^{-2}$ cm$^{-1}$ range. In addition, the reflectivity, R, of sample 12 must be determined either by measurement or by the utilization of published results. Knowing $\beta$ and R (assume same reflectivity on input and output surfaces, 28 and 30, respectively), the absorbed power/transmitted power is given by:

$$(P_{abs}/P_t) = 1/1 - R \, [\exp(\beta l) - (1-R) - R\exp(-\beta l)]$$

where $l$ is the length of sample 12.

The output voltage (Vout) and transmitted power ($P_t$) are measured at least once, with optimum results requiring several measurements and the ratio (Vout/$P_t$) / ($P_{abs}/P_t$) is calculated for each position, the reciprical being $P_{abs}$/Vout.

(6) Select a wavelength for beam 18 at which the surface absorption curve 34 can be measured. That is, a wavelength where the bulk absorption coefficient is larger than approximately 100cm$^{-1}$. In that instance all incident power is abosrbed in the first few tenths of millimeter or less.

(7) The functional dependence (shape) of the surface absorption curve 34 is now determined. This is accomplished by measuring the output voltage, Vout, from detection system 24 versus the distance from beam 18 to transducer 14 at the wavelength selected in step (6). Furthermore, the absorbed power, Pabs, must be determined by measuring the incident power and the power reflected from sample 12. The absorbed power, Pabs, is equal to the incident power minus the reflected power. Surface absorption curve 34 is now derived by plotting Vout/Pabs versus distance.

(8) Since we selected a wavelength where all the power was absorbed, Vout/Pabs (or Pabs/Vout) determined in step (7) is also the calibration factor for surface absorption.

(9) It is now possible to determine simultaneously the bulk and surface absorption coefficients of a sample 12 at any desirable wavelength and having extremely low bulk and surface absorption coefficients. A light beam (laser beam 18) at the wavelength of interest is incident on the sample 12. Referring to FIGS. 1 and 5 of the drawing, the output voltage, distance of beam 18 from transducer 14, and the transmitted power are measured. The signal from the unattached transducer 26 is also measured and subtracted from the signal generated by transducer 14. The net output voltage, Vnet, (voltage from transducer 14 minus voltage from transducer 26) is now divided by the transmitted power, $P_t$, and (Vnet/$P_t$) is plotted versus distance resulting in the combination of a bulk and surface absorption curve 36 shown in FIG. 5.

(10) From the bulk absorption curve 32 (shown in FIG. 2) and derived in step (4) it is known that there is a position 38 where there is zero output voltage due to bulk absorption. At point 38 the net voltage (Vnet) observed in step (9) is only due to surface absorption. Thus, we now know Vout(surf)/P (point 40 in FIG. 2).

(11) We can now generate the surface absorption curve 42 in FIG. 5 for the wavelength of interest, that is Vnet(surf)/$P_t$ versus distance. This can be accomplished since we know the functional dependence (shape) of the surface absorption curve 34 from FIG. 2 (step 7) and we know the position of one point 40 (shown in FIG. 2) now point 44 in FIG. 5.

(12) Calculation of the value of the surface absorption coefficient $\beta_s$ at the wavelength of interest is performed by the following expression:

$$\beta_s = \frac{1-R}{2-R} \frac{Vnet(surf)}{P_t} \left(\frac{Pabs}{Vout}\right)_{calib.}$$

For small R and small bulk absorption where (Pabs/Vout)$_{calib.}$ was found in step (7) and (Vnet(surf))/$P_t$ was found in step (11). It should be noted that the calibration factor and the value of (Vnet(surf))/$P_t$ must be taken at the same position. This expression gives absorption per surface. Assume equal absorption at input and output surfaces 28 and 30, respectively.

(13) We can now generate the bulk absorption curve 46 for the wavelength of interest, that is (Vnet(bulk))/$P_t$ versus distance. This is accomplished by algebraically subtracting (Vnet(surf))/($P_t$) found in step (11) from the experimentally generated combination curve 36 determined in step (9).

(14) Calculation of the value of the bulk absorption coefficient $\beta$ at the wavelength of interest is performed as follows:

$$\frac{Pabs}{P_t} = \frac{Vnet(bulk)}{P_t} \left(\frac{Pabs}{Vout}\right)_{calib}$$

If $\beta l << 1$ then we get $$\beta = \frac{1}{l}\left(\frac{1-R}{1+R}\right) \frac{Vnet(bulk)}{P_t} \left(\frac{Pabs}{Vout}\right)_{calib}$$

As noted before, (Vnet(bulk))/$P_t$ and the calibration factor found in step (5) must be taken at the same position.

The method of this invention is therefore capable of reliably determining low values for $\beta_s$ and $\beta_a$ at any desired wavelength of interest.

Although this invention has been described with reference to a particular procedure, it will be understood to those skilled in the art that this invention is also capable of a modified procedure within the spirit and scope of the appended claims. For example, it is not necessary to generate the entire curve 36 in step (9). In principle it is only necessary to establish Vnet/$P_t$ at the zero-crossing point and at one other point where the bulk absorption has been calibrated. However, by generating the complete curve 36 better accuracy is obtained. In addition, the absorption of coatings, for instance, antireflection coatings and protective coatings can also be measured with the technique of this invention. In such a case, the surface absorption is actually the absorption in the coating.

I claim:

1. A method for simultaneously determining small bulk and surface absorption coefficients in a solid sample comprising the steps of:
   (1) placing said solid sample in optical alignment with a laser beam emanating from a laser;
   (2) attaching a transducer to one surface of said solid sample, said transducer being capable of providing data in order to yield substantially different functional dependent curves of bulk and surface absorption based on voltage divided by power versus distance of said transducer to said laser beam;
   (3) placing means adjacent said sample for detecting the amount of power transmitted through said sample;
   (4) attaching means to said transducer for measuring the output voltage of said transducer;
   (5) passing a first laser beam through said sample, said first laser beam being selected at a wavelength where the bulk absorption is the dominant absorption mechanism and the bulk absorption coefficient can be determined by conventional means;
   (6) measuring the output voltage of said transducer, Vout, said transmitted power, $P_t$, and the distance, $d$, between said first laser beam and said transducer;
   (7) determining the functional dependence of said bulk absorption curve by plotting Vout/$P_t$ versus $d$;
   (8) determining a bulk absorption calibration factor by calculating the absorbed power, Pabs, from the known bulk absorption coefficient and taking the ratio Vout/Pabs;

(9) passing a second laser beam through said sample, said second laser beam being selected at a wavelength where all incident power is absorbed by said sample in the first few tenths of millimeters;

(10) measuring the output voltage of said transducer, Vout, the absorbed power, Pabs, and the distance, $d$, between said second laser beam and said transducer;

(11) determining the functional dependence of said surface absorption curve by plotting Vout/Pabs versus $d$ which then also determines the surface absorption calibration factor;

(12) passing a third laser beam through said sample, said third laser beam being at any desired wavelength wherein the surface and bulk absorption coefficients are unknown;

(13) measuring the output voltage of said transducer, Vout, the transmitted power, $P_t$, and the distance, $d$, between said third laser beam and said transducer;

(14) determining the combined surface and absorption curve by plotting Vout/$P_t$ versus $d$;

(15) generating the surface absorption curve for said third laser wavelength by utilizing a point where said voltage measured in step 13 is due only to surface absorption, said point being determined from step 7 at a distance where said Vout is zero;

(16) generating the bulk absorption curve for said third laser wavelength by algebraically subtracting the surface absorption curve generated in step 15 from the combined surface and absorption curve found in step 14; and

(17) calculating the surface and bulk absorption coefficients from the data obtained from the surface and bulk absorption curves generated in steps 15 and 16, respectively, and the calibration factors determined in steps 8 and 11, respectively.

2. A method for simultaneously determining small bulk and surface absorption coefficients in a solid sample as defined in claim 1 wherein another transducer is placed in the immediate vicinity of said sample in order to detect scattered radiation and said output voltage is determined by subtracting the output voltage from said transducer in the vicinity of said sample from the output voltage from said attached transducer.

3. A method for simultaneously determining small bulk and surface absorption coefficients in a solid sample as defined in claim 2 wherein said surface absorption coefficient is given by the expression:

$$\beta_s = \frac{1-R}{2-R} \frac{Vnet(surf)}{P_t} \left(\frac{Pabs}{Vout}\right)_{calib}$$

where R is the reflectivity of the sample, (Vnet(surf))/$P_t$ is provided by the surface absorption curve generated in step 15, and (Pabs/Vout)$_{calib}$ is the calibration factor determined in step 11.

4. A method for simultaneously determining small bulk and surface absorption coefficients in a solid sample as defined in claim 2 wherein said bulk absorption coefficient is given by the expression:

$$\beta = \frac{1}{l} \left(\frac{1-R}{1+R}\right) \frac{Vnet(bulk)}{P_t} \left(\frac{Pabs}{Vout}\right)_{calib}$$

where $l$ is the length of said sample, R is the reflectivity of said sample, (Vnet(bulk))/$P_t$ is provided by the bulk absorption curve generated in step 16, and (Pabs/Vout)$_{calib}$ is the calibration factor determined in step 8.

* * * * *